(12) United States Patent  (10) Patent No.: US 8,172,821 B2
Flannery  (45) Date of Patent: May 8, 2012

(54) PERSONAL WEAR ABSORBENT ARTICLE WITH WAIST ADJUSTMENT TAB

(75) Inventor: John E. Flannery, Shiocton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 582 days.

(21) Appl. No.: 12/130,468

(22) Filed: May 30, 2008

(65) Prior Publication Data

US 2009/0299317 A1    Dec. 3, 2009

(51) Int. Cl.
*A61F 13/15* (2006.01)
(52) U.S. Cl. ................... 604/391; 604/392; 604/386
(58) Field of Classification Search .......... 604/385.03, 604/386–387, 389–392
See application file for complete search history.

(56) References Cited

U.S. PATENT DOCUMENTS

| | | |
|---|---|---|
| 3,848,594 A | 11/1974 | Buell |
| 4,041,203 A | 8/1977 | Brock et al. |
| 4,374,888 A | 2/1983 | Bornslaeger |
| 4,581,772 A | 4/1986 | Smith |
| 4,663,220 A | 5/1987 | Wisneski et al. |
| 4,766,029 A | 8/1988 | Brock et al. |
| 4,846,815 A | 7/1989 | Scripps |
| 4,869,724 A | 9/1989 | Scripps |
| 4,894,060 A | 1/1990 | Nestegard |
| 4,938,753 A | 7/1990 | Van Gompel et al. |
| 4,940,464 A | 7/1990 | Van Gompel et al. |
| 4,946,527 A | 8/1990 | Battrell |
| 4,988,346 A | 1/1991 | Pfefferkorn |
| 5,019,073 A | 5/1991 | Roessler et al. |
| 5,046,272 A | 9/1991 | Vogt et al. |
| 5,104,116 A | 4/1992 | Pohjola |
| 5,108,384 A | 4/1992 | Goulait |
| 5,169,706 A | 12/1992 | Collier, IV et al. |
| 5,176,670 A | 1/1993 | Roessler et al. |
| 5,176,671 A | 1/1993 | Roessler et al. |
| 5,213,881 A | 5/1993 | Timmons et al. |
| 5,224,405 A | 7/1993 | Pohjola |

(Continued)

FOREIGN PATENT DOCUMENTS

EP    0217032    4/1987

(Continued)

OTHER PUBLICATIONS

International Search Report & Written Opinion for PCT/IB2009/051785, dated Jan. 5, 2010, 9 pages.

*Primary Examiner* — Lynne Anderson
(74) *Attorney, Agent, or Firm* — Armstrong Teasdale LLP

(57) ABSTRACT

An absorbent article includes a front waist region, a back waist region and a crotch region interconnecting the front and back waist regions. An article fastening system attaches the back waist region to the front waist region to define a wear configuration of the absorbent article having a waist opening and a pair of leg openings. The waist opening has a size in the wear configuration of the article. A waist adjustment system includes a tab having an attachment region for attaching the tab to one of the front waist region and the back waist region and a tab region extending transversely outward from the attachment region. The tab region has a fastener region releasably attachable to multiple locations on the one of the front waist region and the back waist region to selectively alter the size of the waist opening in the wear configuration of the article.

30 Claims, 13 Drawing Sheets

U.S. PATENT DOCUMENTS

| | | | |
|---|---|---|---|
| 5,226,992 | A | 7/1993 | Morman |
| 5,242,436 | A | 9/1993 | Weil et al. |
| 5,279,604 | A | 1/1994 | Robertson et al. |
| 5,399,219 | A | 3/1995 | Roessler et al. |
| 5,403,302 | A | 4/1995 | Roessler et al. |
| 5,423,789 | A | 6/1995 | Kuen |
| 5,464,688 | A | 11/1995 | Timmons et al. |
| 5,531,732 | A * | 7/1996 | Wood .......................... 604/391 |
| 5,554,143 | A | 9/1996 | Roe et al. |
| 5,593,401 | A | 1/1997 | Sosalla et al. |
| 5,605,735 | A | 2/1997 | Zehner et al. |
| 5,611,789 | A | 3/1997 | Seth |
| 5,624,428 | A | 4/1997 | Sauer |
| 5,624,429 | A | 4/1997 | Long et al. |
| H001674 | H | 8/1997 | Ames et al. |
| 5,766,389 | A | 6/1998 | Brandon et al. |
| 5,797,896 | A | 8/1998 | Schmitz |
| 5,858,515 | A | 1/1999 | Stokes et al. |
| 6,030,373 | A | 2/2000 | VanGompel et al. |
| 6,063,066 | A | 5/2000 | Inoue et al. |
| 6,174,303 | B1 | 1/2001 | Suprise et al. |
| 6,264,644 | B1 | 7/2001 | Igaue et al. |
| 6,287,287 | B1 | 9/2001 | Elsberg |
| 6,302,871 | B1 | 10/2001 | Nakao et al. |
| 6,322,552 | B1 | 11/2001 | Blenke et al. |
| 6,371,949 | B1 | 4/2002 | Soga et al. |
| 6,402,731 | B1 | 6/2002 | Suprise et al. |
| 6,454,752 | B1 | 9/2002 | Huang et al. |
| 6,491,675 | B1 | 12/2002 | Shimada et al. |
| 6,508,797 | B1 | 1/2003 | Pozniak et al. |
| 6,524,293 | B1 | 2/2003 | Elsberg et al. |
| 6,544,242 | B1 | 4/2003 | Kido et al. |
| 6,551,294 | B1 | 4/2003 | Elsberg et al. |
| 6,572,601 | B2 | 6/2003 | Suprise et al. |
| 6,595,977 | B1 | 7/2003 | Luizzi, Jr. et al. |
| 6,648,866 | B2 | 11/2003 | Magee et al. |
| 6,682,512 | B2 | 1/2004 | Uitenbroek et al. |
| 6,736,804 | B1 | 5/2004 | Robertson et al. |
| 6,849,067 | B2 | 2/2005 | Fletcher et al. |
| 6,893,426 | B1 | 5/2005 | Popp et al. |
| 6,916,750 | B2 | 7/2005 | Thomas et al. |
| 6,932,802 | B2 | 8/2005 | Luizzi, Jr. et al. |
| 6,945,968 | B2 | 9/2005 | Svensson et al. |
| 6,972,012 | B1 | 12/2005 | Pozniak et al. |
| 6,994,697 | B2 | 2/2006 | Shimada et al. |
| 7,150,730 | B2 | 12/2006 | Hasler et al. |
| 7,150,733 | B2 | 12/2006 | Yamakawa et al. |
| 7,156,833 | B2 | 1/2007 | Couture-Dorschner et al. |
| 7,175,584 | B2 | 2/2007 | Maxton et al. |
| 7,189,220 | B2 | 3/2007 | Miyoshi et al. |
| 7,198,621 | B2 | 4/2007 | Moser et al. |
| 7,201,744 | B2 | 4/2007 | Van Gompel et al. |
| 7,207,979 | B2 | 4/2007 | Price et al. |
| 7,211,072 | B2 | 5/2007 | Nawata et |
| 7,473,818 | B2 * | 1/2009 | Datta et al. .................... 604/366 |
| 7,568,264 | B2 | 8/2009 | Miyamoto et al. |
| 2002/0032427 | A1 | 3/2002 | Schmitz et al. |
| 2002/0138059 | A1 | 9/2002 | Van Gompel et al. |
| 2002/0165518 | A1 | 11/2002 | Datta et al. |
| 2002/0173768 | A1 | 11/2002 | Elsberg et al. |
| 2003/0153891 | A1 | 8/2003 | Molee |
| 2004/0122400 | A1 | 6/2004 | Hancock et al. |
| 2004/0236301 | A1 | 11/2004 | Wendelstorf et al. |
| 2005/0090793 | A1 | 4/2005 | Winqvist |
| 2006/0069376 | A1 | 3/2006 | Miller |
| 2006/0069378 | A1 | 3/2006 | Winkel et al. |

FOREIGN PATENT DOCUMENTS

| | | | |
|---|---|---|---|
| EP | 1600132 | A1 * | 11/2005 |
| EP | 1829513 | A2 | 9/2007 |
| GB | 2185383 | A | 7/1987 |
| GB | 2284742 | A | 6/1995 |
| JP | 8005691 | Y2 | 2/1996 |
| JP | 2003079666 | A | 3/2003 |
| WO | 9746197 | A1 | 12/1997 |
| WO | 0027328 | A1 | 5/2000 |
| WO | 0037009 | | 6/2000 |
| WO | 0188245 | | 11/2001 |

* cited by examiner

PERSONAL WEAR ABSORBENT ARTICLE WITH WAIST ADJUSTMENT TAB

BACKGROUND

The present invention relates generally to absorbent articles intended for personal wear, and more particularly to disposable absorbent articles.

Absorbent articles intended for personal wear, e.g., diapers, training pants, feminine hygiene products, adult incontinence products, bandages, medical garments and the like are designed to take in and at least temporarily retain body waste. Diapers, as an example, are typically placed and secured on a wearer using a set of primary fastening tabs, such as adhesive tabs or mechanical (e.g., hook or loop) fastening system tabs, and left in place to absorb insults as well as to contain fecal waste. With the primary fastening tabs secured, the diaper includes a waist opening for receiving the waist of the wearer and a pair of leg openings for receiving the respective legs of the wearer.

The size of the waist opening of diapers is often adjustable using the primary fastening tabs. In one known embodiment, the fastening tabs include a pair of spaced hook fastening components attached to a back waist region of the diaper and a loop fastening component (e.g., a patch of loop material) having a length and being disposed on a front waist region of the diaper for receiving the hook fastening components. Typically, the hook fastening components may be pulled around the respective hips of the wearer and attached generally anywhere to the loop fastening component to selectively choose the size of the waist opening of the diaper. As a result, the waist opening can be selected to comfortably fit the wearer of the diaper when initially placing the diaper on the wearer by choosing the locations on that loop component to which the hook components are fastened.

The fastening tabs provided on diapers are relatively small in the longitudinal direction of the diapers. Rather, they are typically much longer in the transverse direction because, as mentioned above, they are used for pulling the back of the diaper around the wearer and fastening to the front of the diaper. The sides of the diaper are relatively short in length (e.g., from waist opening to leg opening) so control of the sides of the diaper is simple using the small (in the longitudinal direction) fastening tabs provided on diapers.

Training pants, unlike diapers, typically come pre-assembled to more closely resemble conventional underpants. In particular, the front and back waist regions of the pants are attached either permanently or refastenably (such as by a primary fastening system). The sides of training pants, however, are typically much longer from the waist opening to the leg openings and therefore more difficult to manipulate with a tab as small as those used on diapers.

Moreover, the relatively small longitudinal direction of the fastening tabs of conventional training pants limits the range of adjustability of the training pants using the fastening tabs. Typically, the adjustability of waist openings of training pants is provided by elastic waist members in the form of an elastic waist band. Thus, the range of adjustability of the waist opening is limited directly by stretchability of the elastic waist members and of the components of the pants to which the members are attached.

As a result, there is a need for a personal wear article that has a wider range of adjustability in the waist opening of the absorbent article.

SUMMARY

In one aspect, an absorbent article for personal wear about a wearer's waist generally comprises a central absorbent assembly comprising a liquid permeable inner layer for facing the wearer, an outer layer for facing away from the wearer, an absorbent body disposed therebetween, a front waist region, a back waist region and a crotch region extending longitudinally between and interconnecting the front and back waist regions. An article fastening system attaches the back waist region to the front waist region to define a wear configuration of the absorbent article having a waist opening and a pair of leg openings spaced from the waist opening. The waist opening has a size in the wear configuration of the article. A waist adjustment system comprises a tab having an attachment region for attaching the tab to one of the front waist region and the back waist region and a tab region extending transversely outward from the attachment region. The tab region has a fastener region releasably attachable to multiple locations on the one of the front waist region and the back waist region to selectively alter the size of the waist opening in the wear configuration of the article.

In another aspect, an absorbent article for personal wear about a wearer's waist generally comprising a liquid permeable bodyside liner for facing the wearer, an outer cover for facing away from the wearer, an absorbent body disposed between the liner and the outer cover, a front waist region, a back waist region and a crotch region extending longitudinally between and interconnecting the front and back waist regions. A pair of laterally opposite front side panels extends outward from the front waist region. A pair of laterally opposite back side panels extends outward from the back waist region. The back side panels and front side panels cooperatively define respective sides of the article. A primary fastening system for releasably attaching the side panels extends outward from the front waist region to respective side panels extending outward from the back waist region. A waist adjustment system comprises a tab having an attachment region for attaching the tab to one of the front side panels and the back side panels and a tab region extending transversely outward from the attachment region. The tab region has a fastener region releasably attachable to multiple locations on the one of the front side panel and the back side panel to selectively alter the size of the waist opening.

In yet another aspect, a waist adjustment system for an absorbent article for personal wear about a wearer's waist generally comprises a liquid permeable bodyside liner for facing the wearer, an outer cover for facing away from the wearer, an absorbent body disposed between the liner and the outer cover, a front waist region, a back waist region and a crotch region extending longitudinally between and interconnecting the front and back waist regions. An article fastening system attaches the back waist region to the front waist region to define a wear configuration of the absorbent article having a waist opening and a pair of leg openings spaced from the waist opening. The waist opening has a size in the wear configuration of the absorbent article. The waist adjustment system generally comprises a tab having an attachment region for attaching the tab to one of the front waist region and the back waist region and a tab region extending transversely outward from the attachment region. The tab region has a fastener region releasably attachable to multiple locations on the one of the front waist region and the back waist region to selectively alter the size of the waist opening in the wear configuration.

Other features of the invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION OF THE DRAWINGS

Figure 1:
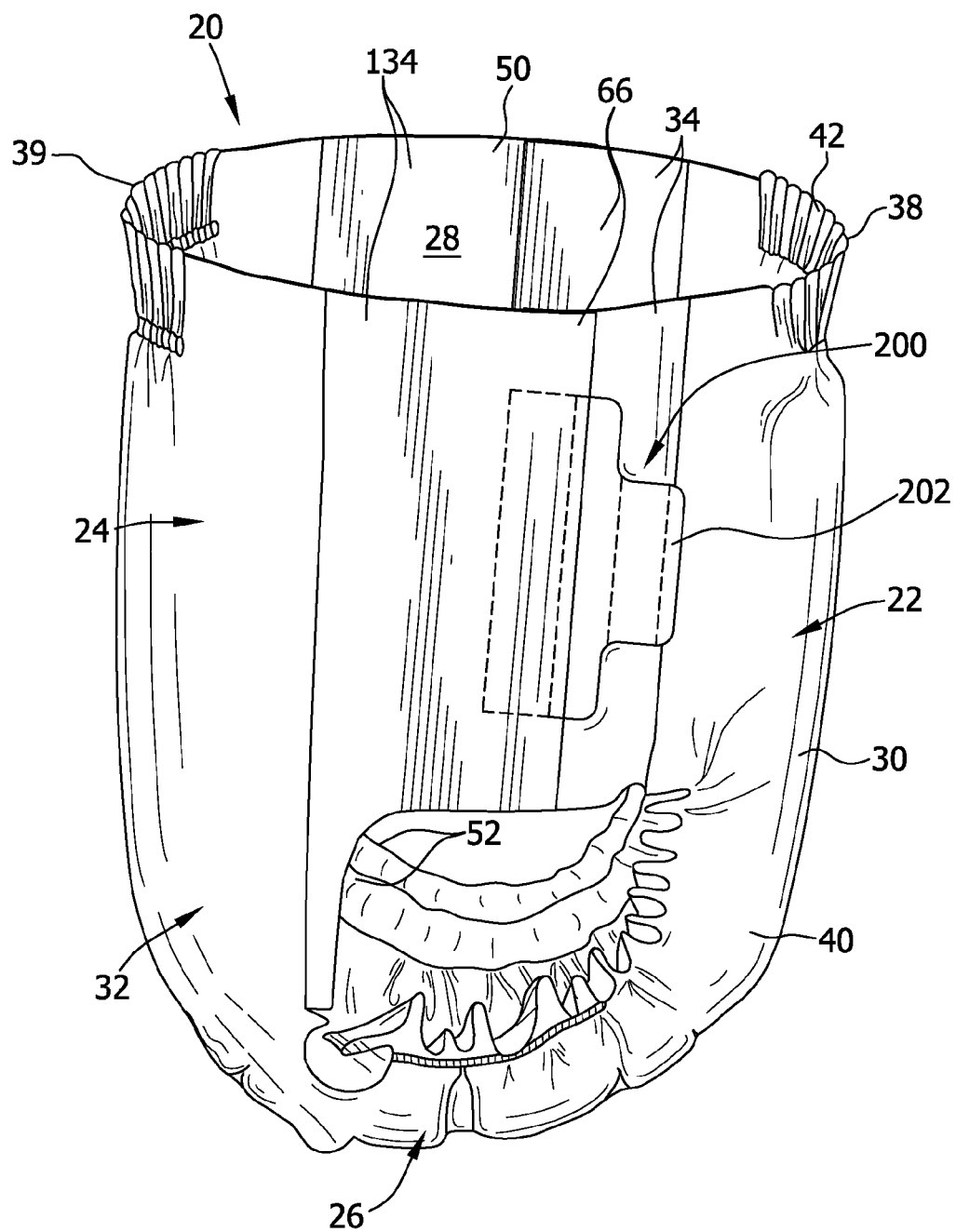
FIG. 1 is a side perspective of one embodiment of a personal wear article in the form of a pair of training pants having a waist adjustment tab.

Referring now to the drawings and in particular to FIG. 1, a personal wear absorbent article according to one embodiment is illustrated in the form of a pants-type article for wear about a wearer's waist, and more particularly in the form of children's toilet training pants, indicated in its entirety by the reference numeral 20. The term absorbent generally refers to articles that may be placed against or in proximity to the body of the wearer to absorb and/or retain various liquid wastes discharged from the body. The absorbent article may or may not be disposable, which refers to articles that are intended to be discarded after a limited period of use instead of being laundered or otherwise restored for reuse. It is understood that the concepts described herein are suitable for use with various other pants-type articles such as adult incontinence articles, as well as other articles intended for personal wear such as clothing, diapers, feminine hygiene products, medical garments, surgical pads and bandages, other personal care or health care garments, and the like without departing from the scope of the present invention.

By way of illustration only, various materials and methods for constructing the training pants 20 are disclosed in PCT Patent Application WO 00/37009 published Jun. 29, 2000 by A. Fletcher et al; U.S. Pat. No. 4,940,464 issued Jul. 10, 1990 to Van Gompel et al.; and U.S. Pat. No. 5,766,389 issued Jun. 16, 1998 to Brandon et al., which are incorporated herein by reference.

Figure 2:
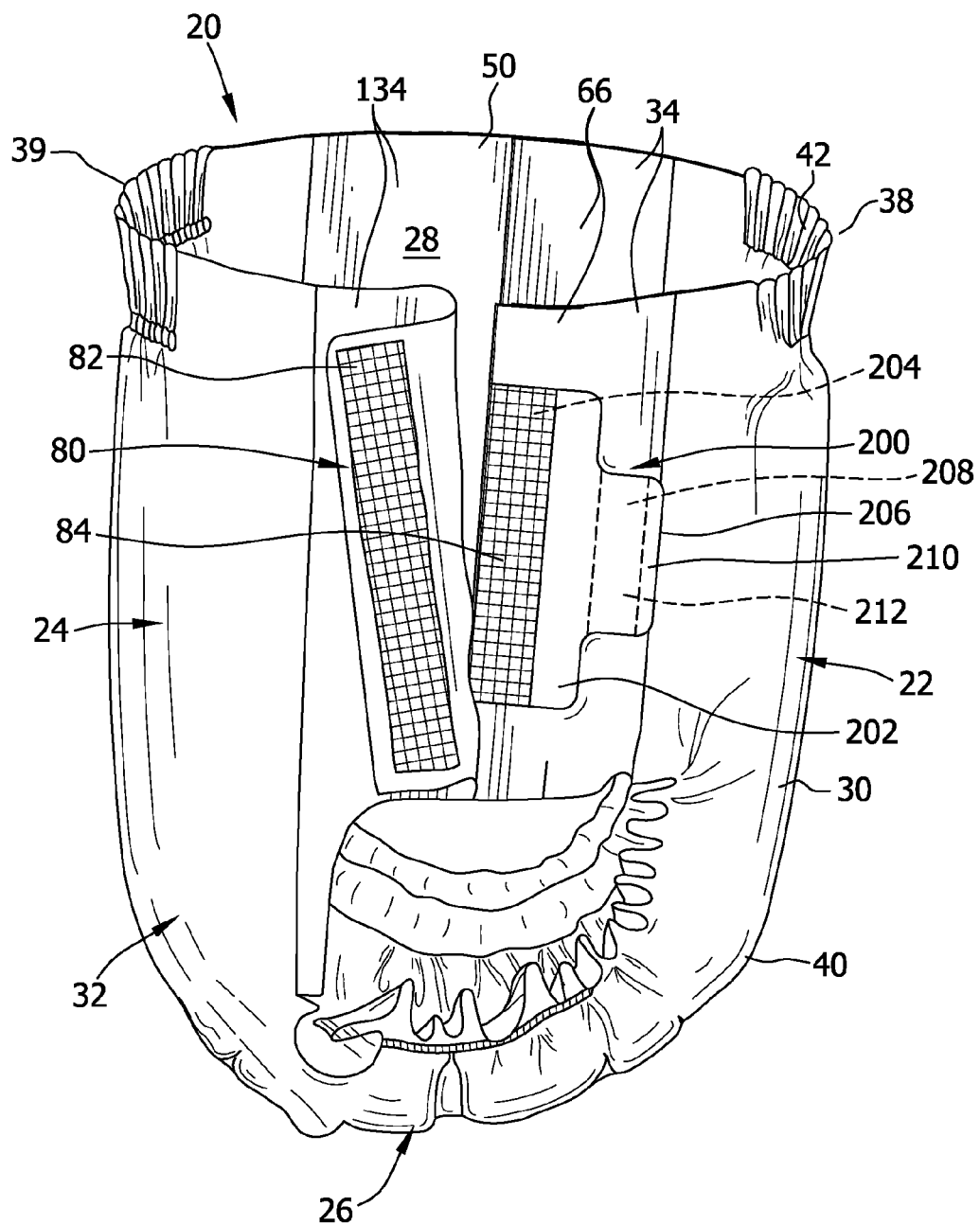
FIG. 2 is a side perspective similar to FIG. 1 with an article fastening system of the training pants in an unfastened condition on one side of the training pants.

The pair of training pants 20 is illustrated in FIG. 1 in a fully pre-assembled (i.e., as assembled during initial manufacture) configuration (broadly referred to herein as a wear configuration of the pants, i.e., absorbent article) and in FIG. 2 in a partially unfastened condition. The training pants 20 comprises a front waist region 22, a back waist region 24, a crotch region 26 extending longitudinally between and interconnecting the front and back waist regions along a longitudinal direction of the pants, an inner surface 28 configured for contiguous relationship with the wearer, and an outer surface 30 opposite the inner surface. With additional reference to FIGS. 3 and 4, the training pants 20 also has a pair of laterally opposite side edges 36 and a pair of longitudinally opposite waist edges, respectively designated front waist edge 38 and back waist edge 39. The front waist region 22 is contiguous with the front waist edge 38, and the back waist region 24 is contiguous with the back waist edge 39.

Figure 3:
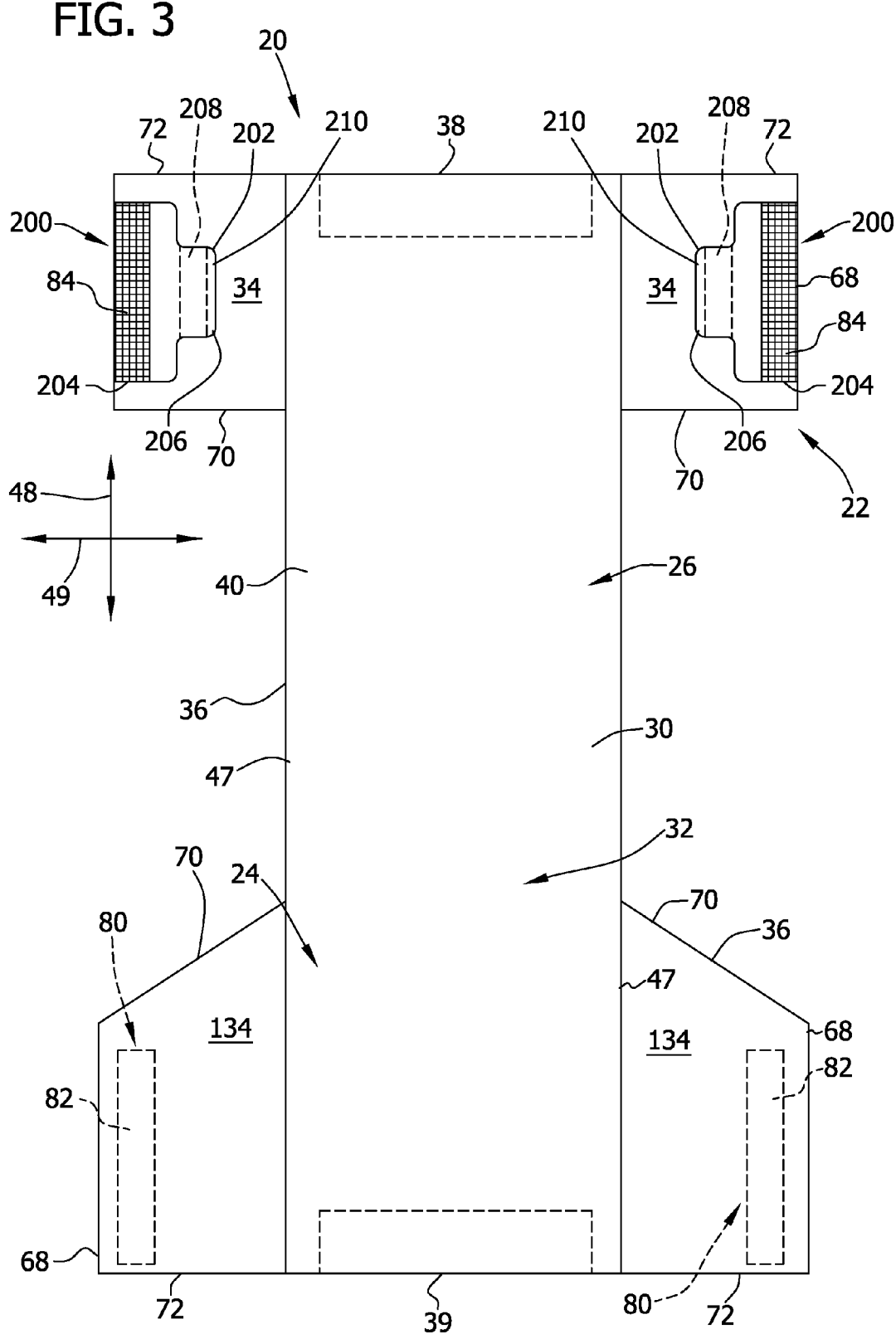
FIG. 3 is a plan view of an outer surface of the training pants of FIG. 1 in an unfastened, unfolded and laid flat condition.
Figure 4:
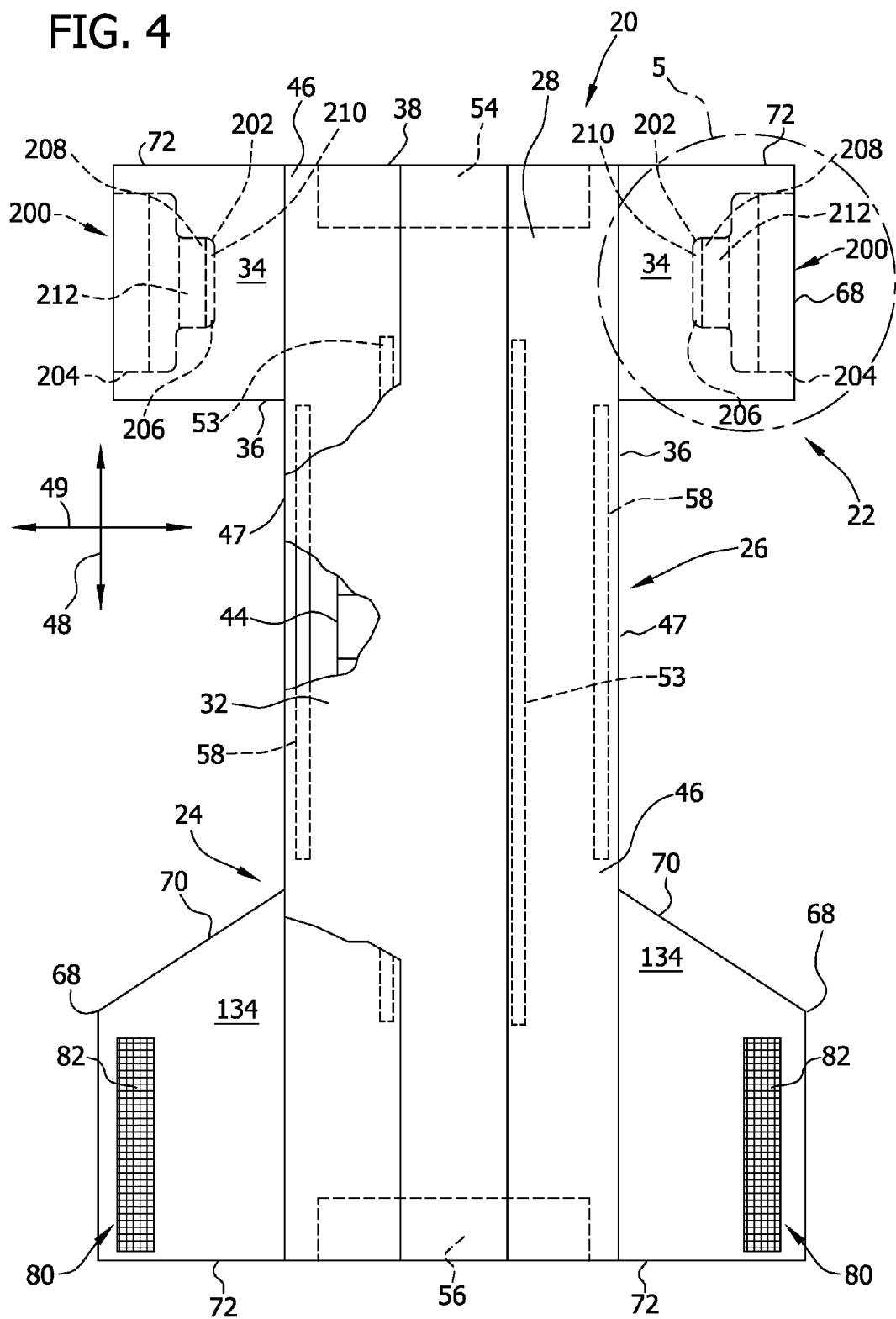
FIG. 4 is a plan view similar to FIG. 3 but showing an inner surface of the training pants, which faces the wearer when worn, and with portions cut away to show underlying features.

The illustrated pants 20 comprises a central absorbent assembly, generally indicated at 32, which when laid flat as in FIGS. 3 and 4 can be rectangular or any other desired shape. A pair of laterally opposite front side panels 34 extends outward from the absorbent assembly 32 at the front waist region 22 (thereby forming transversely outer portions of the front waist region, and more broadly in part forming transversely opposite sides of the training pants). Laterally opposite back side panels 134 extend outward from the absorbent assembly 32 at the back waist region 24 (thereby forming transversely outer portions of the back waist region, and together with the front side panels 34 further defining the sides of the pants).

The central absorbent assembly 32 of the illustrated embodiment comprises an outer cover 40 and a bodyside liner 42 (FIGS. 2 and 4) connected to the outer cover in a superposed relation by suitable means such as adhesives, ultrasonic bonds, thermal bonds or other conventional techniques. An absorbent structure 44 (FIG. 4) is disposed between the outer cover and the bodyside liner. A pair of containment flaps 46 (FIG. 4) is secured to the bodyside liner 42 for inhibiting the lateral flow of body exudates. The central absorbent assembly 32 has opposite ends which form portions of the front and back waist edges 38 and 39, and opposite side edges 47 which form portions of the side edges 36 of the training pants 20 (FIGS. 3 and 4).

The absorbent assembly 32 and side panels 34, 134 may comprise two or more separate elements, as shown in FIGS. 1 and 2, or they may be integrally formed. Integrally formed side panels 34, 134 and absorbent assembly 32 would comprise at least some common materials, such as the bodyside liner, flap composite, outer cover, other materials and/or combinations thereof, and could define a one-piece elastic, stretchable, or nonstretchable pants 20. For further reference, arrows 48 and 49 in FIGS. 3 and 4 depict the orientation of a longitudinal axis and a transverse or lateral axis, respectively, of the training pants 20.

With the training pants 20 in the fastened condition as illustrated fully in FIG. 1 and partially in FIG. 2, the front and back side panels 34, 134 are attached to each other by a primary, or article fastening system 80 to define the pre-assembled three-dimensional wear configuration of the pants, having a waist opening 50 and a pair of leg openings 52. The front waist region 22 comprises the portion of the training pants 20 which, when worn, is positioned at least in part on the front of the wearer while the back waist region 24 comprises the portion of the training pants which is positioned at least in part on the back of the wearer. The crotch region 26 of the training pants 20 comprises the portion of the training pants 20 which is positioned between the legs of the wearer and covers the lower torso of the wearer.

The front and back side panels 34, 134 comprise the portions of the training pants 20 (and more particularly of the front and back waist regions 22, 24) which, when worn, are positioned on the hips of the wearer. The attached side panels 34, 134 thus broadly define the transversely opposite sides of the pants 20, with each side extending a length Lp (FIG. 5) from the waist opening 50 to the respective leg opening 52 at an engagement seam 66 along which the fastening system 80 releasably attaches the front and back side panels. The waist edges 38 and 39 of the training pants 20 are configured to encircle the waist of the wearer and together define the waist opening 50 (FIG. 1). Portions of the side edges 36 in the crotch region 26 generally define the leg openings 52.

The central absorbent assembly 32 is configured to contain and/or absorb exudates discharged from the wearer. For example, the containment flaps 46 are configured to provide a barrier to the transverse flow of body exudates. A flap elastic member 53 (FIG. 4) can be operatively joined with each containment flap 46 in any suitable manner as is well known in the art. The elasticized containment flaps 46 define a partially unattached edge which assumes an upright configuration in at least the crotch region 26 of the training pants 20 to form a seal against the wearer's body. The containment flaps 46 can be located along the side edges 36 of the pants 20, and can extend longitudinally along the entire length of the absorbent assembly 32 or may only extend partially along the length of the absorbent assembly. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pants 20 also suitably includes a front waist elastic member 54 (FIG. 4), a rear waist elastic member 56, and leg elastic members 58, as are known to those skilled in the art. The waist elastic members 54 and 56 (collectively, "a first waist adjustment member") can be attached to the outer cover 40 and/or the bodyside liner 42 along the opposite waist edges 38 and 39, and can extend over part or all of the waist edges. The leg elastic members 58 can be attached to the outer cover 40 and/or the bodyside liner 42 along the opposite side edges 36 and positioned in the crotch region 26 of the training pants 20. The leg elastic members 58 can be longitudinally aligned along each side edge 47 of the absorbent assembly 32.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. In one particular embodiment, for example, the leg elastic members 58 comprise a plurality of dry-spun coalesced multifilament spandex elastomeric threads sold under the trade name LYCRA and available from E. I. Du Pont de Nemours and Company, Wilmington, Del., U.S.A.

The elasticity of the waist elastic members 54, 56 and the leg elastic members 58 allow the waist opening 50 and leg openings 52, respectively, to conform to a range of user sizes. For example, in use, the waist elastic members 54, 65 stretch across the front and back of the wearer's waist thereby holding the training pants 20 snuggly but comfortably against the wearer's waist. The leg elastic members 58 provide the same function for the leg openings 52. That is, the leg elastic members 58 hold the training pants snuggly but comfortably against the wearer's legs. As a result, the waist elastic members 54, 56 and the leg elastic members 58 provide some adjustability in how snug the training pants 20 fits against the waist and legs of the wearer.

The outer cover 40 suitably comprises a material which is substantially liquid impermeable. The outer cover 40 can be a single layer of liquid impermeable material, but more suitably comprises a multi-layered laminate structure in which at least one of the layers is liquid impermeable. For instance, the outer cover 40 can include a liquid permeable outer layer and a liquid impermeable inner layer that are suitably joined together by a laminate adhesive, ultrasonic bonds, thermal bonds, or the like. Suitable laminate adhesives can be applied continuously or intermittently as beads, a spray, parallel swirls, or the like. The liquid permeable outer layer can be any suitable material and is desirably one that provides a generally cloth-like texture. The outer layer may also be made of those materials of which the liquid permeable bodyside liner 42 is made. While it is not a necessity for the outer layer to be liquid permeable, it is suitable that it provides a relatively cloth-like texture to the wearer.

The inner layer of the outer cover 40 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bed sheets and clothing, as well as the wearer and caregiver.

If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. One suitable "breathable" material is composed of a microporous polymer film or a nonwoven fabric that has been coated or otherwise treated to impart a desired level of liquid impermeability.

The liquid permeable bodyside liner 42 is illustrated as overlying the outer cover 40 and absorbent core 44, and may but need not have the same dimensions as the outer cover 40. The bodyside liner 42 is suitably compliant, soft feeling, and non-irritating to the child's skin. Further, the bodyside liner 42 can be less hydrophilic than the absorbent structure 44 to present a relatively dry surface to the wearer and permit liquid to readily penetrate through its thickness. Alternatively, the bodyside liner 42 can be more hydrophilic or can have essentially the same affinity for moisture as the absorbent structure 44 to present a relatively wet surface to the wearer to increase the sensation of being wet. This wet sensation can be useful as a training aid. The hydrophilic/hydrophobic properties can be varied across the length, width and/or depth of the bodyside liner 42 and absorbent structure 44 to achieve the desired wetness sensation or leakage performance.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spun-bonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal center line.

As noted previously, the illustrated training pants 20 have front and back side panels 34 and 134 defining transversely opposite sides of the pants in the wear configuration of the pants. The side panels 34 and 134 can be permanently attached along seams 66 to the central absorbent assembly 32 in the respective front and back waist regions 22 and 24. More particularly, as seen best in FIGS. 2 and 3, the front side panels 34 can be permanently attached to and extend transversely outward beyond the side edges 47 of the absorbent assembly 32 in the front waist region 22, and the back side panels 134 can be permanently attached to and extend transversely outward beyond the side edges of the absorbent assembly in the back waist region 24. The side panels 34 and 134 may be attached to the absorbent assembly 32 using attachment means known to those skilled in the art such as adhesive, thermal, pressure or ultrasonic bonding. Alternatively, the side panels 34 and 134 can be formed as an integral portion of a component of the absorbent assembly 32. For example, the side panels can comprise a generally wider portion of the outer cover 40, the bodyside liner 42, and/or another component of the absorbent assembly 32.

The front and back side panels 34, 134 each have an outer edge 68 spaced laterally from the seam 66, a leg end edge 70 disposed toward the longitudinal center of the training pants 20, and a waist end edge 72 disposed toward a longitudinal end of the training pants. The leg end edge 70 and waist end edge 72 extend from the side edges 47 of the absorbent assembly 32 to the outer edges 68. The leg end edges 70 of the side panels 34 and 134 form part of the side edges 36 of the training pants 20. The leg end edges 70 of the illustrated embodiment are suitably curved and/or angled relative to the transverse axis 49 to provide a better fit around the wearer's legs. However, it is understood that only one of the leg end edges 70 may be curved or angled, such as the leg end edge of the back waist region 24, or neither of the leg end edges may be curved or angled, without departing from the scope of this invention. The waist end edges 72 are suitably parallel to the transverse axis 49. The waist end edges 72 of the front side panels 34 form part of the front waist edge 38 of the training pants 20, and the waist end edges 72 of the back side panels 134 form part of the back waist edge 39 of the pants.

The side panels 34, 134 suitably, although not necessarily, comprise a stretchable material capable of stretching in a direction generally parallel to the transverse axis 49 of the training pants 20. More suitably the side panels 34, 134 comprise an elastic material. Suitable elastic materials, as well as one process of incorporating stretchable side panels into training pants, are described in the following U.S. patents: U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the stretch material may comprise a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the name of Taylor et al.; and PCT application WO 01/88245 in the name of Welch et al.; all of which are incorporated herein by reference.

In one particularly suitable embodiment at least the front side panels 34 and more suitably both the front and back side panels 34, 134 comprise a vertical filament laminate (VFL) material. A VFL is a composite material having at least one gatherable layer such as a non-woven material and at least one elastic layer. The layers are joined together when the elastic layer is extended from its original condition so that upon relaxing the layers, the gatherable layer is gathered. The composite may be stretched to the extent that the non-elastic material gathered between the bond locations allows the elastic material to elongate. One type of vertical filament laminate is disclosed, for example, by U.S. Pat. No. 6,916,750 to Thomas et al., the content of which is incorporated herein by reference in its entirety. More suitably, the front and back side panels comprise a VFL in which two non-woven (gatherable) layers sandwich an elastic layer so that both faces of the VFL are gatherable. The rugosities formed in the gatherable layers of such a VFL material allow the VFL material to be used as a loop component of a fastening system.

Alternatively, the side panel material may comprise other woven or nonwoven materials, such as those described above as being suitable for the outer cover 40 or bodyside liner 42; mechanically pre-strained composites; or stretchable but inelastic materials.

The absorbent structure 44 can be any structure which is generally compressible, conformable, non-irritating to the wearer's skin and capable of absorbing and retaining liquid body exudates, and may be manufactured in a wide variety of sizes and shapes, and from a wide variety of absorbent materials commonly used in the art. For example, the absorbent structure 44 suitably comprises a matrix of absorbent fibers, and more particularly hydrophilic fibers, such as a web of cellulosic fluff. In a particularly suitable embodiment, the absorbent structure 44 comprises a matrix of cellulosic fluff, such as wood pulp fluff, and superabsorbent particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent structure 44 to better contain and absorb body exudates. The concentration of the superabsorbent particles can also vary through the thickness of the absorbent core 44. Alternatively, the absorbent structure 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany.

In one embodiment, the absorbent structure 44 comprises a blend of wood pulp fluff and superabsorbent material. As a general rule, the superabsorbent material is present in the absorbent structure 44 in an amount of from 0 to about 90 weight percent based on total weight of the absorbent assembly. The absorbent structure 44 suitably has a density within the range of about 0.10 to about 0.35 grams per cubic centimeter. The absorbent structure 44 may or may not be wrapped or encompassed by a suitable tissue wrap that may help maintain the integrity and/or shape of the absorbent assembly.

The article fastening system 80 comprises laterally opposite first fastening components 82 adapted for refastenable engagement to corresponding second fastening components 84. In one embodiment, a front or outer surface of each of the fastening components 82, 84 comprises a plurality of engaging elements. The engaging elements of the first fastening components 82 are adapted to repeatedly engage and disengage corresponding engaging elements of the second fastening components 84 to releasably secure the pants 20 in its three-dimensional configuration.

The fastening components 82, 84 can comprise any refastenable fasteners suitable for absorbent articles, such as adhesive fasteners, cohesive fasteners, mechanical fasteners, or the like. In particular embodiments the fastening components 82, 84 comprise mechanical fastening components for improved performance. Suitable mechanical fastening components can be provided by interlocking geometric shaped materials, such as hooks, loops, bulbs, mushrooms, arrowheads, balls on stems, male and female mating components, buckles, snaps, or the like.

In the illustrated embodiment, the first fastening components 82 (i.e., one on each side of the training pants 20) comprise loop fasteners and the second fastening components 84 comprise complementary hook fasteners. Alternatively, the first fastening components 82 may comprise hook fasteners and the second fastening components 84 may comprise complementary loop fasteners. In another embodiment, the fastening components 82, 84 can comprise interlocking similar surface fasteners, or adhesive and cohesive fastening elements such as an adhesive fastener and an adhesive-receptive landing zone or material; or the like. Although the training pants 20 illustrated in FIG. 1 show the back side panels 134 overlapping the front side panels 34 upon connection thereto, which is convenient, the training pants 20 can also be configured so that the front side panels overlap the back side panels when connected. One skilled in the art will recognize that the shape, density and polymer composition of the hooks and loops may be selected to obtain the desired level of engagement between the fastening components 82, 84. A more aggressive hook material may comprise a material with a greater average hook height and/or a greater percentage of directionally-aligned hooks. When engaged, the fastening components 82, 84 of the illustrated embodiment define the refastenable engagement seams 66 (FIG. 2).

In one particularly suitable embodiment, as best seen in FIGS. 2 and 4, the loop fastening components 82 are formed separate from the back side panels 134 and attached thereto, such as by adhesive, thermal bonds, ultrasonic bonds, pressure bonds or other suitable techniques. It is understood, however, that the back side panels 134 may be constructed so that the inner surfaces of the respective back side panels define loop fastening components 82 (i.e., the back side panels 134 and fastening components 82 are formed integrally) without departing from the scope of this invention.

With particular reference now to FIGS. 1 and 2, a waist adjustment system, generally indicated at 200, is provided for use in adjusting (FIGS. 7 and 7A) the size of the waist opening 50 of the pants 20 as described in further detail later herein. As illustrated in FIGS. 1-3, the waist adjustment system 200 comprises a waist adjustment tab 202 attached to each of the front side panels 34 (broadly, to the transversely opposite sides of the training pants 20). As seen best in FIG. 5, each tab 202 comprises an attachment region 204 at which the tab is attached to the respective front side panel 34, and a tab region 206 extending transversely outward from the attachment region. The attachment region 204 of each tab 202 is suitably attached to the respective front side panel 34 (broadly, to the respective side of the pants 20) and in the illustrated embodiment is attached to the outer surface of the front side panel.

In the illustrated embodiment, the second fastening components 84 of the article fastening system 80 is adhered (or otherwise attached) to the waist adjustment tab 202 generally at the attachment region 204 thereof. More particularly, the attachment region 204 and second fastening component 84 are coextensive. It is understood, however, that the attachment regions 204 of the waist adjustment tabs 202 and second fastening components 84 of the article fastening system 80 can be spaced or otherwise offset from each other. As seen in FIG. 3, the attachment regions 204 and the second fastening components 84 are disposed adjacent respective transverse edges of the front side panels 34. Each of the waist adjustment tabs 202 extends from the attachment region 204 toward the longitudinal centerline of the pants 20. As a result, no portion of the waist adjustment tabs 202 extends beyond the extent of the respective front side panel 34. In other words, the entire waist adjustment tab 202 overlies the front side panel 34 to which it is attached.

The attachment region 204 of each tab 202 is suitably attached to the outer surface of the front side panel 34, such as by adhesive, thermal bonding, ultrasonic bonding, pressure bonding or other suitable attachment technique. The tab region 206 of each tab 202 extends transversely outward of the attachment region 204 into overlapping relationship with the outer surface of the corresponding front side panel 34 (e.g., further toward the central absorbent assembly 32) so that the tab region is accessible exterior of the pants 20 when the pants are worn. It is understood, however, that the tab region 206 may instead extend transversely to opposed relationship with and be releasably attachable to the outer surface of the back side panel 134 without departing from the scope of this invention.

The tab region 206 of the tab 202 comprises at least one fastener region 208 having a fastening component 212 for use in securing the tab region to the front side panel 34, and may further comprise a grip region 210 transversely outward of the fastener region for use in manually gripping and manipulating the tab relative to the pants 20. The fastening component 212 of the illustrated fastener region 208 comprises a hook fastener, and the outer surface of each front side panel 34 suitably defines a corresponding fastening component, e.g., a loop fastener, to permit the tab 202 on each side of the pants 20 to be attached at its fastener region to the respective front side panel (i.e., broadly, to the pants). For example, the front side panel 34 in one particularly suitable embodiment may be constructed of VFL material as described previously so that the outer surface of the front side panel itself defines a loop fastening component. Alternatively, a loop fastener component (not shown) may be formed separate from the front side panel 34 and attached to the panel outer surface without departing from the scope of this invention.

The outer facing surface 30 of the outer cover 40 of the pants 20 is also suitably constructed to define a loop fastener, such as by forming the outer cover of a material that defines a loop fastening component (e.g., VFL or other suitable material) or by forming a separate loop fastening component and attaching it to the outer surface of the pants outer cover, to permit attachment of the tab 202 to the outer cover.

Figure 5:
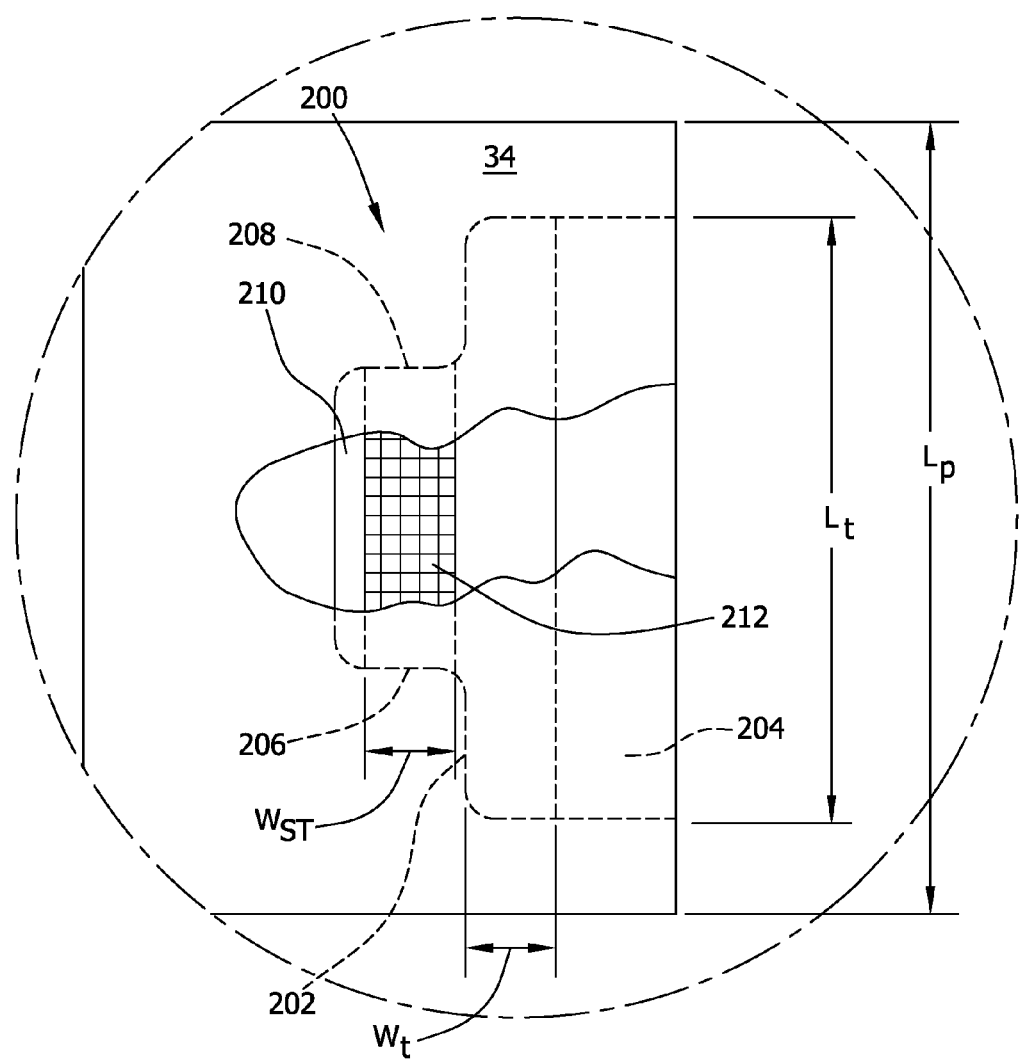
FIG. 5 is a an enlarged fragmented view of the encircled area of FIG. 4.

It is understood that the fastening component(s) 212 defining the one or more fastener regions 208 of the tab 202 may instead be a loop fastener component, with the outer surfaces of the front side panels 34 and outer cover 40 of the pants 20 being constructed to define corresponding hook fastening components. In other embodiments, the fastening component 212 defining the tab fastener region(s) 208 and the outer surfaces of the front side panels 34 and pants outer cover 40 may comprise other suitable releasably attachable fasteners without departing from the scope of this invention. With reference to FIG. 5, the fastener region 208 of each tab 202 suitably extends lengthwise of the tab, within the tab region 206 thereof, to the edges of the tab at the tab region. It is understood, however, that the fastener region 208 need not extend the full length of the tab 202 at the tab region 206 to remain within the scope of this invention.

The tab region 206 of each tab 202, i.e., the portion of the tab that extends transversely outward from the attachment region 204 (and in the illustrated embodiment comprises the fastener region 208 and a grip region 210 of the tab). When the tab 202 includes the grip region 210, such as in the illustrated embodiment of FIGS. 1-4, the tab is suitably constructed so that the grip region is non-attachable to the pants (i.e., the absorbent article). The term non-attachable as used in this instance means that the grip region 210 is not releasably or otherwise removably attachable to the pants in the wear configuration thereof, nor is the grip region permanently attached to the pants. In one embodiment, the grip region 210 extends transversely outward from the fastener region 208 of each tab 202 to provide sufficient unattached material of the tab for readily gripping and pulling on the tab.

Figure 6:
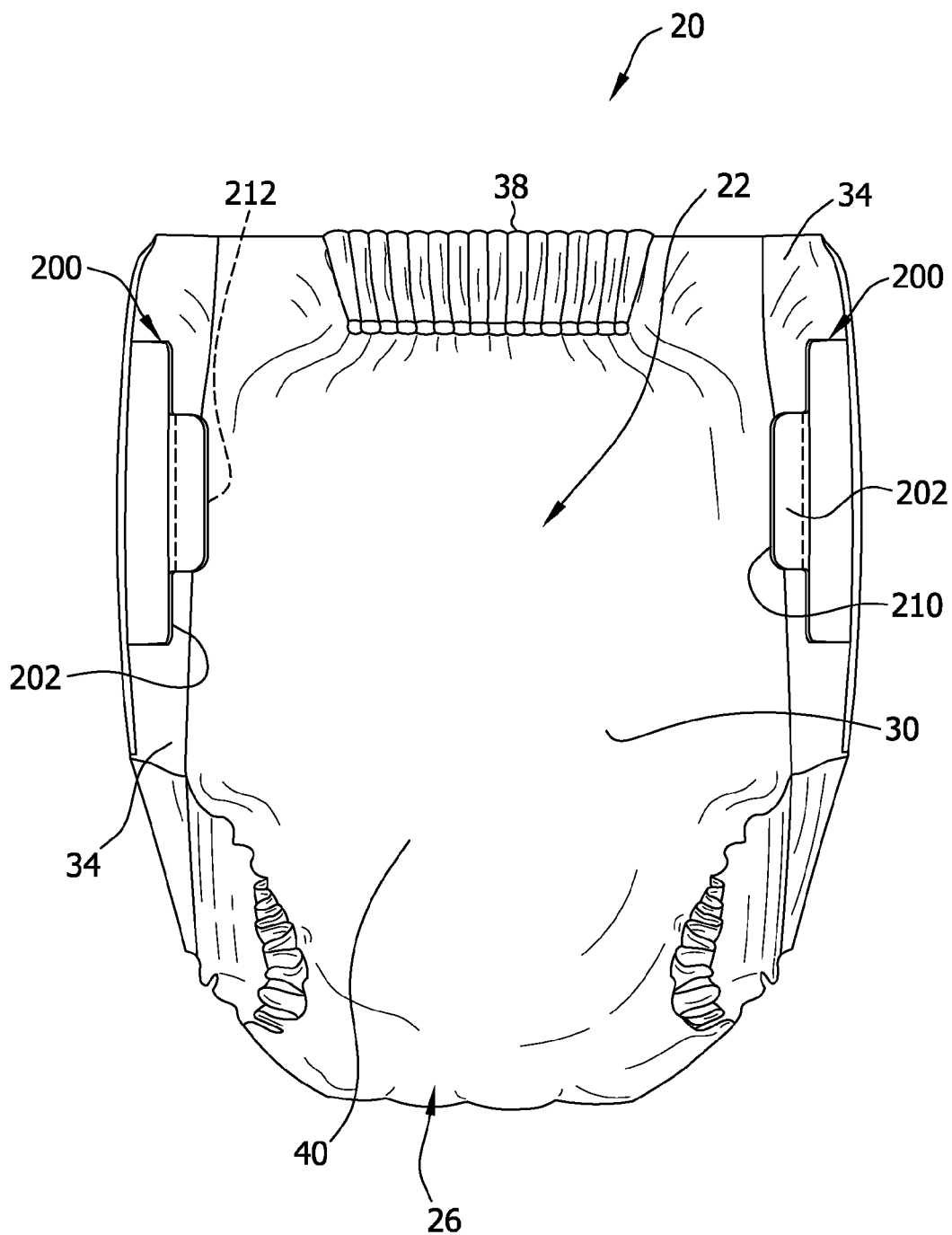
FIG. 6 is a front perspective of the training pants showing the waist adjustment tabs in a relaxed, wear configuration of the pants.
Figure 7:
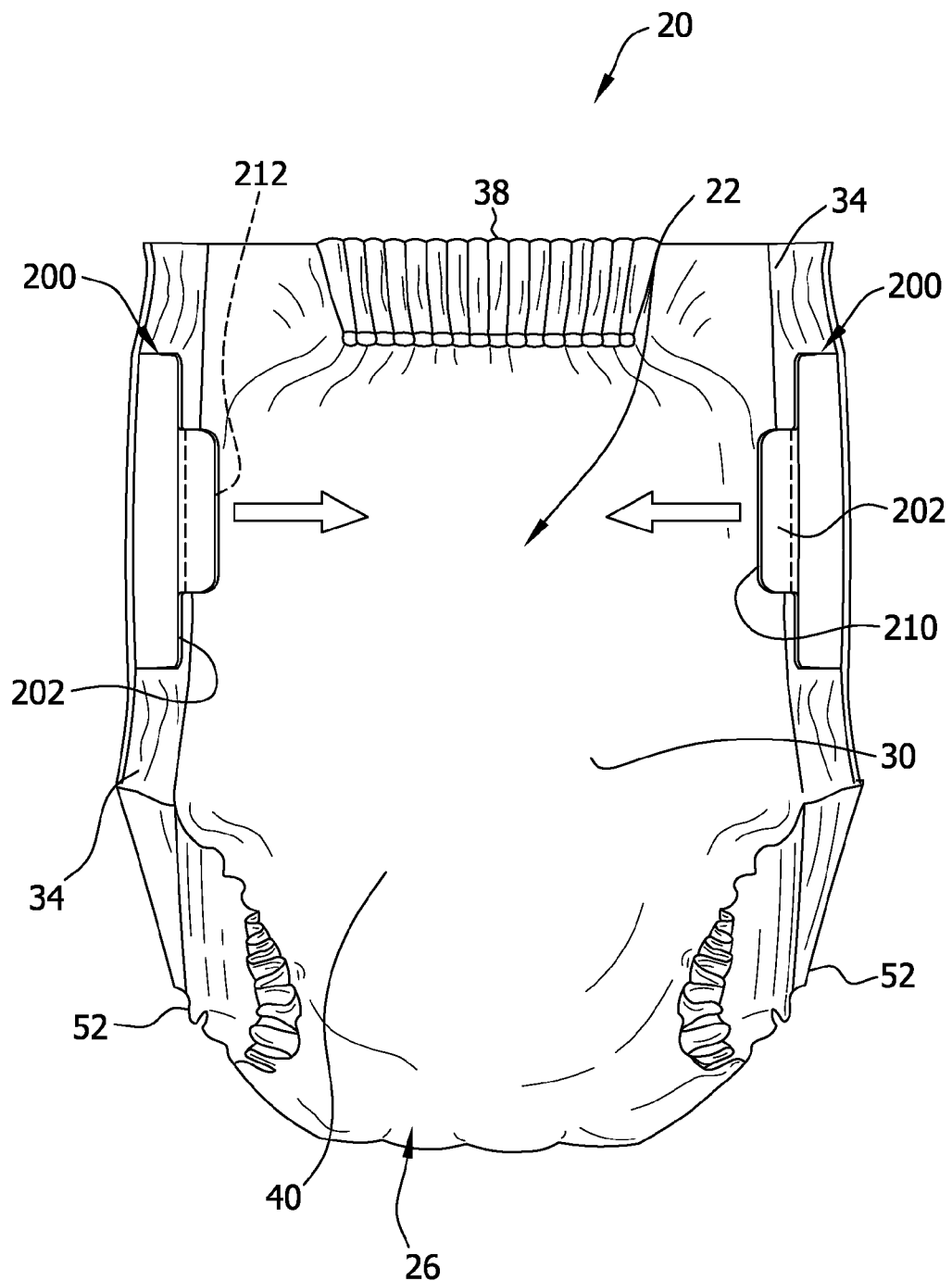
FIG. 7 is a front perspective similar to FIG. 6 but showing the waist adjustment tabs in a fitted, wear configuration of the pants.
Figure 7A:
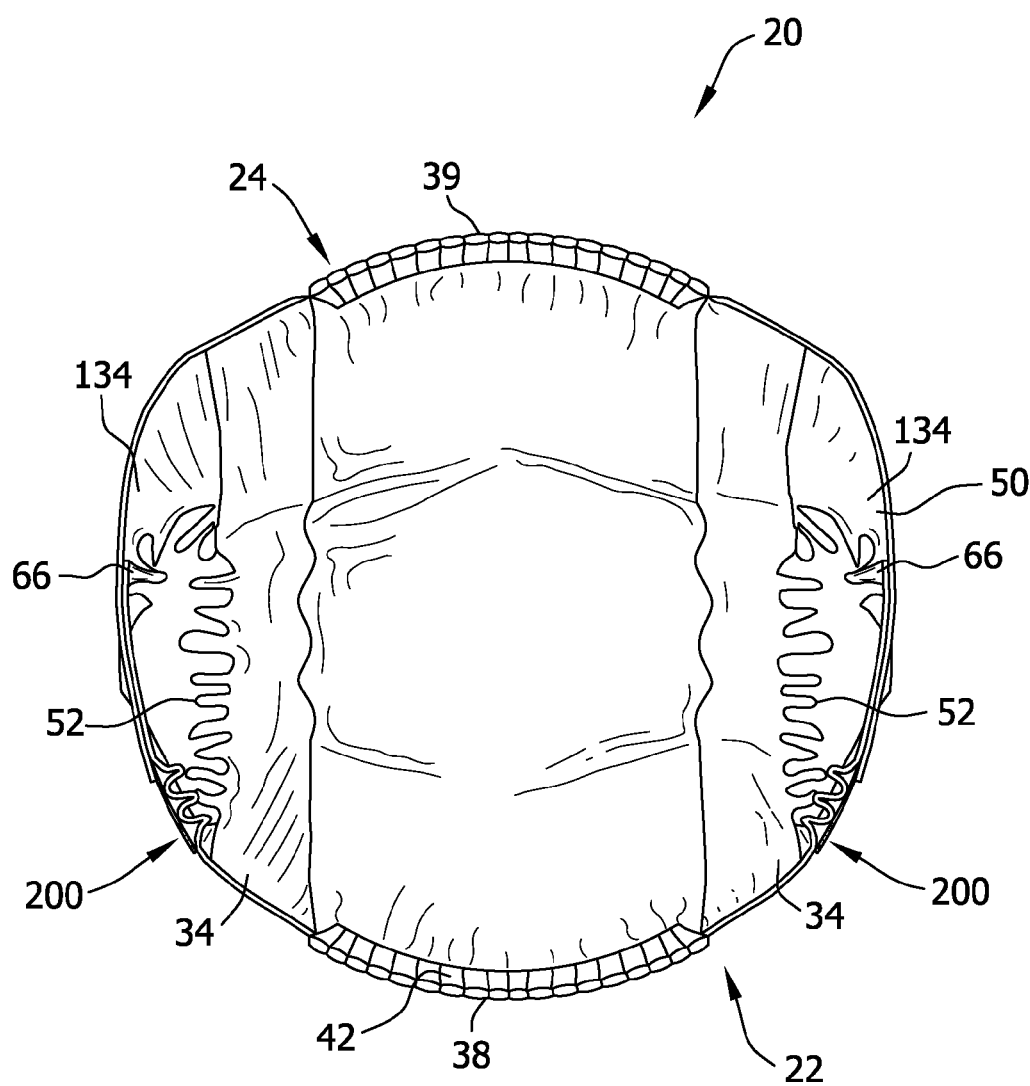
FIG. 7A is a top plan view of the training pants shown in FIG. 7.

As illustrated in FIGS. 6 and 7, the waist adjustment system 200 can be used to adjust the size of the waist opening 50 of the pants. FIG. 6 illustrates the pants 20 in a relaxed, wear configuration. In this configuration, the size of the waist opening 50 is maximized so that the pants 20 can be easily put on or taken off of the wearer. FIGS. 7 and 7A, however, illustrate the pants 20 in a fitted, wear configuration. In this configuration, the waist adjustment system 200 has been manually manipulated to conform the size of the waist opening 50 of the pants to the specific wearer or to at least reduce the size of the waist opening. The waist opening 50 size can be decreased, for example, by grasping the grip region 210 of one or both of the tabs 202 and pulling them transversely toward the longitudinal axis of the pants 20 at the first waist region as illustrated by the arrows in FIG. 7. In this configuration, one or both of the front side panels 34 are cinched or otherwise gathered to reduce the size of the waist opening 50.

In one suitable embodiment, the tab 202 is less stretchable (at least in the transverse direction thereof) than the component of the pants 20 to which it is attached and, more suitably, the tab is non-stretchable. In one particularly suitable embodiment, the tab 20 may comprise spunbond/meltblown/spunbond (SMS) laminates and/or spunbond/meltblown (SM) laminates. Various examples of suitable SMS laminates are described in U.S. Pat. No. 4,041,203 to Brock et al.; U.S. Pat. No. 5,213,881 to Timmons, et al.; U.S. Pat. No. 5,464,688 to Timmons, et al.; U.S. Pat. No. 4,374,888 to Bornslaeger; U.S. Pat. No. 5,169,706 to Collier, et al.; and U.S. Pat. No. 4,766,029 to Brock et al., which are incorporated herein in their entirety by reference to the extent they are consistent herewith.

In use, the training pants 20 are constructed and pre-assembled in their relaxed, wear configuration, with the article fastening system 80 releasably attaching the front and back waist regions 22, 24 (and more particularly the front and back side panels 34, 134 in the illustrated embodiment). The fastener region 208 of each tab 202 is releasably attached to the outer surface of the respective front side panel 34 to releasably attach the tab 202 to the pants 20.

With the pants in their relaxed, wear configuration, the pants 20 can be put on the wearer in the same manner as underwear. That is, the wearer can place each leg through the respective leg openings 52 and pull the pants upward to place the waist opening 50 adjacent the wearer's waist. If needed, the size of the waste opening 50 can be reduced using the waist adjustment system 200. In other words, waist adjustment system 200 can be used to manually manipulate the size of the waist opening 50 to conform the size of the waist opening of the pants 20 to the specific wearer. As mentioned above, the size of the waist opening 50 can be decreased by grasping the grip region 210 of one or both of the tabs 202 and pulling them upward away from the front side panel 34 to unfastening the fastener region 208 from the front side panel and inward toward the longitudinal axis of the pants 20 as illustrated by the arrows in FIG. 7. In this configuration, one or both of the front side panels 34 are cinched or otherwise gathered to reduce the size of the waist opening. With the front side panels cinched, the tabs 202 are pressed against the front side panel 34 to refasten the fastener region 208 of the tab to the front side panel and thereby secure the front side panels in their cinched position.

Figure 8A:
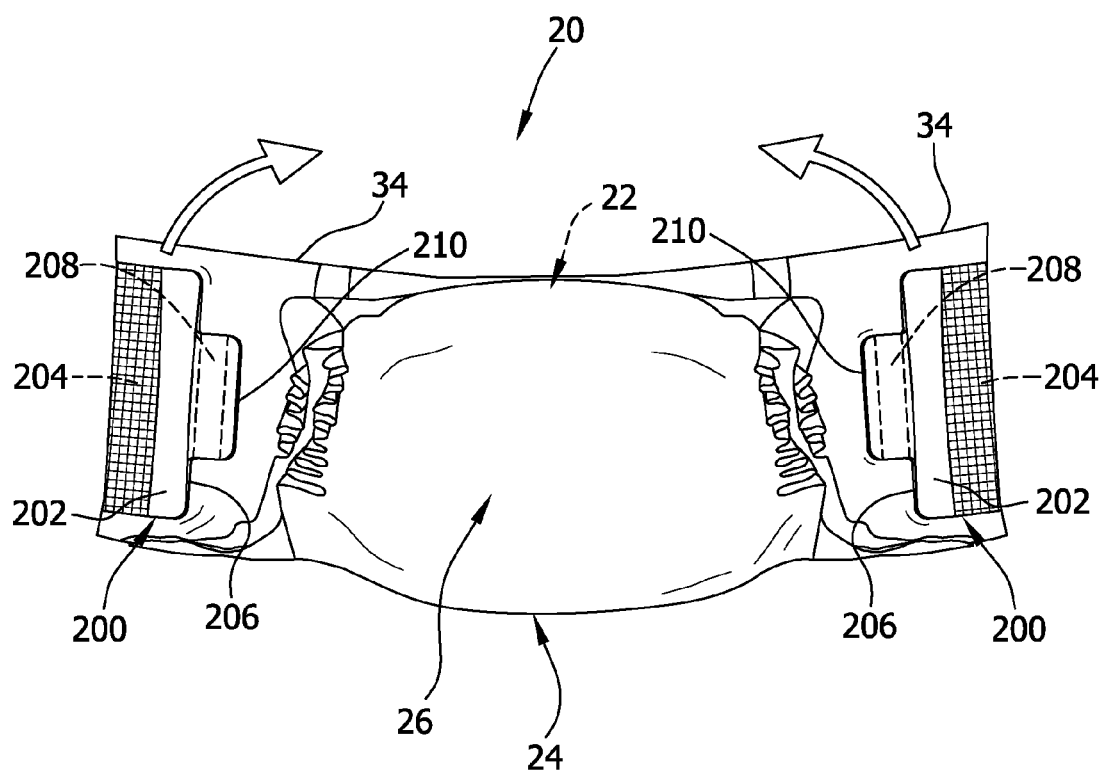
FIG. 8A is a schematic of the training pants of FIG. 1 in a partially compacted disposal configuration.

When the pants 20 are to be discarded after use, the pants may be slipped off of the wearer in the manner of conventional underpants, or the front and back waist regions 22, 24 may be detached from each other (e.g., by separation of the fastening components 82, 84 of the article fastening system 80) and the pants removed from the wearer. To dispose of the used pants 20, the pants are laid on a surface with the back waist region 24 down against the surface and with the front and back waist regions 22, 24 in opposed relationship with each other. The sides, and more particularly the front and back side panels 34, 134 in the illustrated embodiment, suitably extend transversely outward in opposed relationship with each other. With reference to FIG. 8A, the crotch region 26 and a portion of the back waist region 24 of the pants 20 are then folded or rolled up over the front waist region 22 of the pants. If not already done, the tab regions 206 of the tabs 202 are gripped at the grip regions 210 thereof and are pulled away from the pants 20 to detach the fastener region 208 of the tabs from the pants (i.e., from the front side panels 34 in the illustrated embodiment). While gripping the detached tab regions 206 of the tabs 202, the tabs are pulled around the folded or rolled portion of the pants 20 and then toward each other as indicated by the direction arrows in FIG. 8A.

Figure 8B:
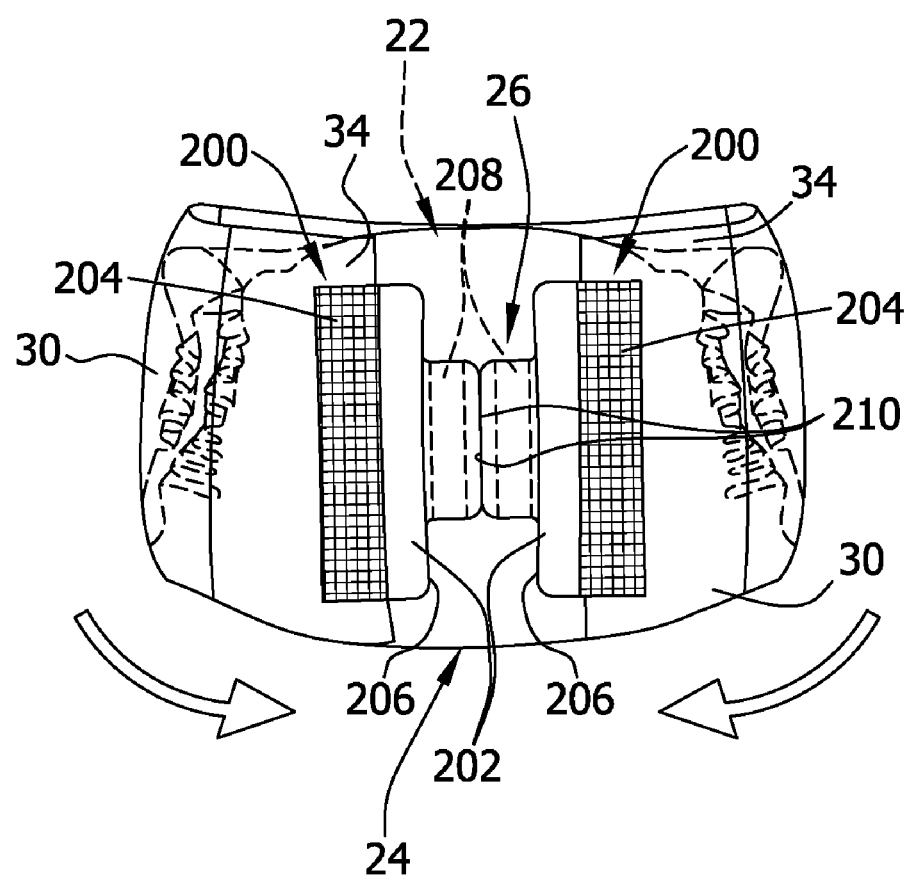
FIG. 8B is a schematic of the training pants of FIG. 8A in a fully compacted disposal configuration with the waist adjustment tabs in a fastened condition to secure the pants in the disposal configuration.

The fastener regions 208 of the tabs 202 are attached to the folded or rolled portion of the pants 20 (i.e., to the outer surface 30 of the back waist region or of the crotch region of the pants) to thereby secure the pants in their compact disposal configuration as illustrated in FIG. 8B. In this configuration, the pants 20 are relatively compact and held generally tightly in this compact configuration to reduce the risk of leakage from the pants.

While in FIG. 8B the tabs 202 are brought into positions generally adjacent each other to secure the pants 20 in the disposal configuration thereof, it is contemplated that one of the tabs may be pulled across the longitudinal centerline of the pants and secured thereto (e.g., to the outer surface 30 of the pants), and then the other tab pulled across the longitudinal centerline over and beyond the one tab and secured to the pants, such as the back side panel 134 to which the one tab is attached since it is of a VFL material, to provide a further compacted disposal configuration of the pants.

Figure 9A:
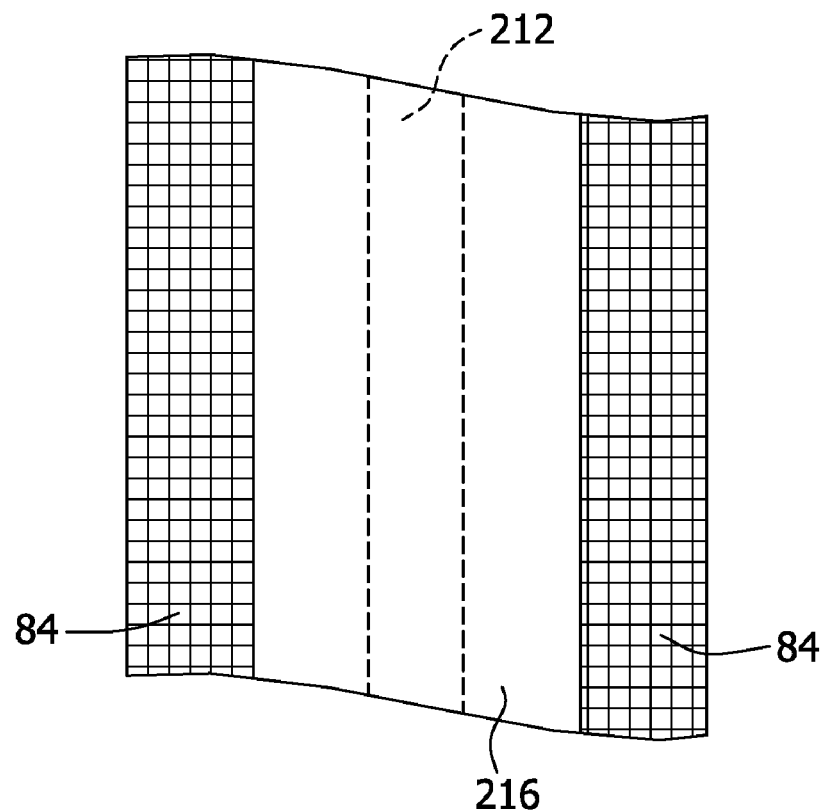
FIG. 9A is a top plan view of a segment of a continuous web comprising a substrate and a plurality of fastener elements attached to the substrate.
Figure 9B:
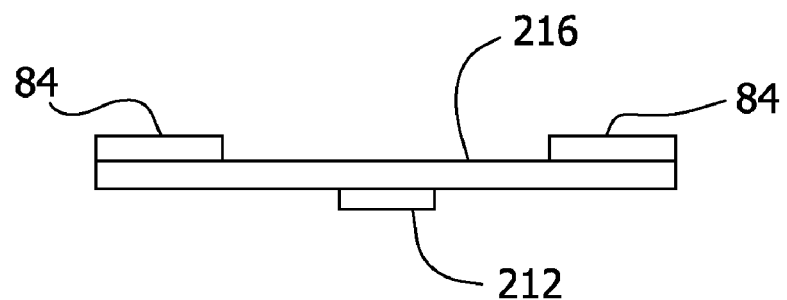
FIG. 9B is an end view of the segment of the continuous web shown in FIG. 9A.
Figure 10:
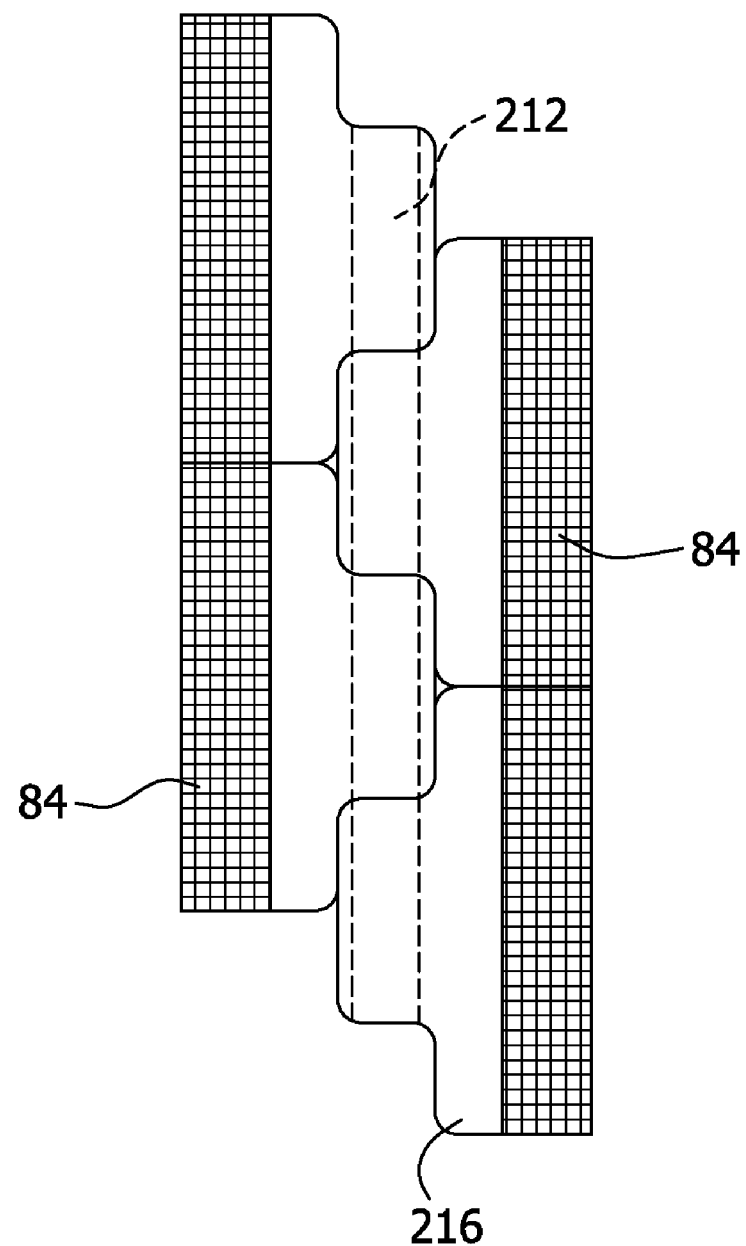
FIG. 10 is a top plan of the segment of the continuous web after having passed through a die to form a plurality of waist adjustment tabs therefrom.
Figure 11:
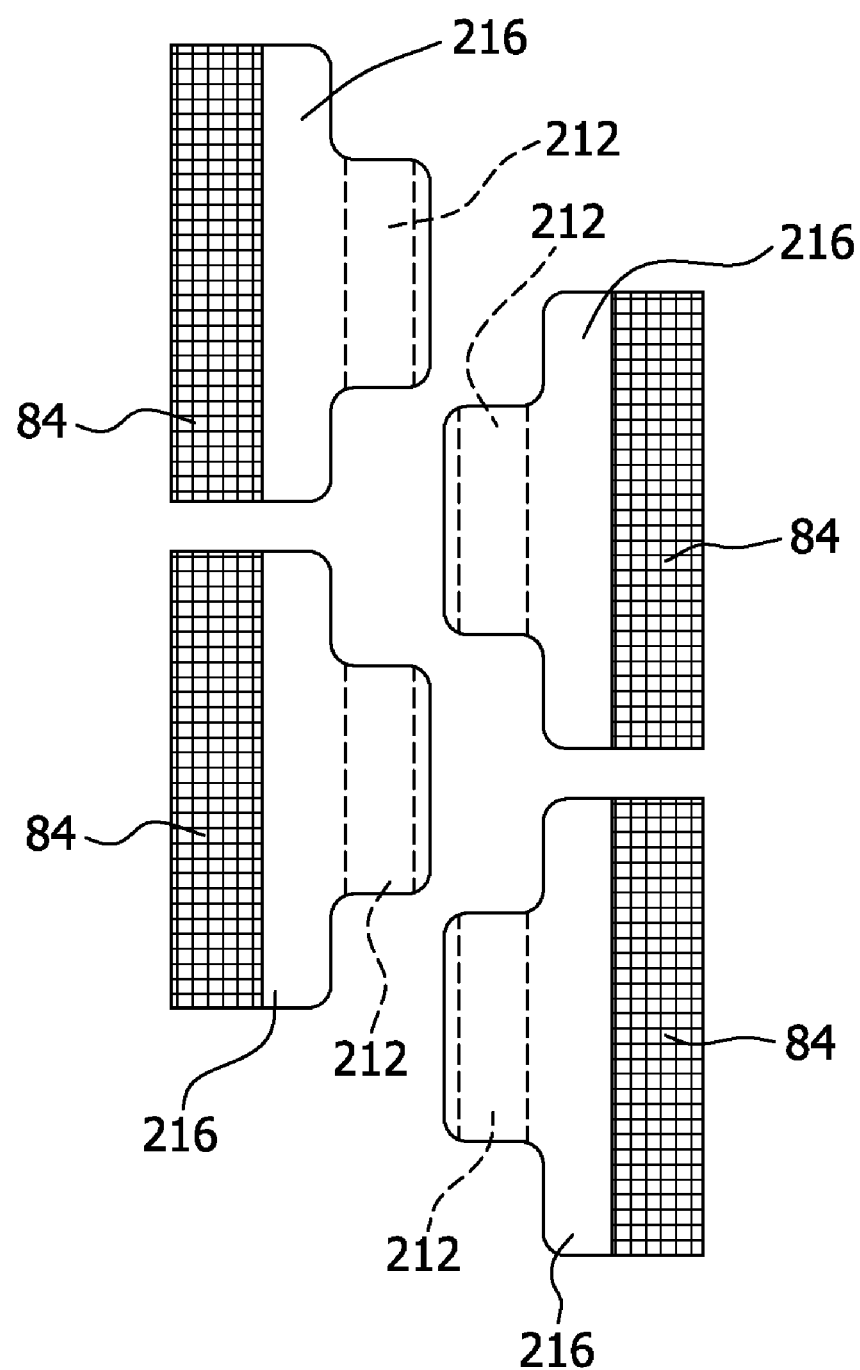
FIG. 11 is a top plan similar to FIG. 10 but illustrating the plurality of waist adjustment tabs separated from one another.

In one suitable embodiment illustrated in FIGS. 9A and 9B, a plurality of the waist adjustment tabs 202 may be suitably constructed from a continuous web (e.g., a substrate) 216 having the fastening component 212 (e.g., hook fastener material in the illustrated embodiment) of the fastener region 208 and the second fastening component of the article fastening system attached thereto such as by adhesive bonding, thermal bonding, ultrasonic bonding, pressure bonding or other suitable technique to define the fastener region of the disposal tab. In one embodiment, a first web of hook fastener material for forming the fastening component 212 of the fastener region 208 is attached generally along a longitudinal axis of the substrate 216 and a second web of hook material for forming the second fastening component of the article fastening system is spaced from the first web and bonded to the surface of the continuous web opposite the first web of hook fastener material. That is, one web of hook material is attached to one side (e.g., a first surface) of the continuous web and another web of hook material is attached to the opposite side (e.g., a second surface) of the continuous web. In a particularly suitable embodiment, which is illustrated in FIGS. 9A and 9B, a third web of hook material for forming the second fastening component of the article fastening system is spaced from the first web and bonded to the opposite surface (second surface) of the continuous web than the first web. After the three webs of hook material are attached to the continuous web, the continuous web is contacted by a die or other suitable cutting apparatus to cut the waist adjustment tabs from the continuous web (FIGS. 10 and 11).

After the waist adjustment tabs 202 are cut from the continuous web, the tabs are attached to the front side panels 34 of the pants 20 adjacent the transverse edges thereof, as illustrated in FIG. 3. FIG. 3 is representative of a suitable configuration (i.e., laid flat) in which the article would be conveyed during the final steps of processing, such as, fastening of the article fastening system and folding of the pants. As shown, the entire waist adjustment tab 202 overlies the respective front side panel 34 to which it is attached. Moreover, the fastener region 208 of the tab 202 can be releasably secured to front side panel 34. That is, the fastening component 212 (e.g., hooks) of fastener region 208 can be secured to the loops of the front side panel 34. As a result, the waist adjustment tab 202 does not interfere with or otherwise impede the final steps of processing.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. An absorbent article for personal wear about a wearer's waist, said article comprising:
    a central absorbent assembly comprising a liquid permeable inner layer for facing the wearer, an outer layer for facing away from the wearer, an absorbent body disposed therebetween, a front waist region, a back waist region and a crotch region extending longitudinally between and interconnecting the front and back waist regions;
    an article fastening system attaching the back waist region to the front waist region to define a wear configuration of the absorbent article having a waist opening and a pair of leg openings spaced from the waist opening, the waist opening having a size in the wear configuration of the article; and
    a waist adjustment system comprising a tab having an attachment region which attaches the tab to one of said front waist region and said back waist region and a tab region extending transversely outward from the attachment region, the tab region having a fastener region releasably attachable to multiple locations on said one of said front waist region and said back waist region to selectively alter the size of the waist opening in said wear configuration of the article, wherein the fastener region of the tab is attached to said one of said front waist region and said back waist region when said front waist region and said back waist region are detached at said article fastening system.

2. The absorbent article as set forth in claim 1 further comprising a pair of front side panels, the tab attachment region being attached to one of said front side panels.

3. The absorbent article as set forth in claim 2 wherein the fastener region of the tab is releasably attachable to the front side panel to which the tab is attached.

4. The absorbent article as set forth in claim 3 wherein at least a portion of the front side panel to which the tab is attached is cinched upon reducing the side of the waist opening in the wear configuration of the article.

5. The absorbent article as set forth in claim 1 wherein the tab region of the tab comprises a grip region disposed outward of the fastener region for use in manually gripping and manipulating the tab.

6. The absorbent article as set forth in claim 5 wherein the waist adjustment system comprises two spaced-apart tabs.

7. The absorbent article as set forth in claim 1 wherein the article can be configured in a compact disposal configuration, the fastener region of the tab being releasably attachable to one of said back waist region and said crotch region to secure the article in its compact disposal configuration.

8. The absorbent article as set forth in claim 1 wherein the article fastening system is operable independent of the waist adjustment system.

9. The absorbent article as set forth in claim 1 wherein a portion of the article fastening system overlays a portion of the waist adjustment system.

10. The absorbent article as set forth in claim 1 wherein a portion of the waist adjustment system underlies the article fastening system.

11. The absorbent article as set forth in claim 1 wherein the article fastening system releasably attaches the back waist region to the front waist region in overlapping relationship to define the wear configuration of the absorbent article.

12. The absorbent article as set forth in claim 1 wherein the article fastening system attaches the back waist region to the front waist region along an engagement seam, the engagement seam extending generally from the waist opening to one of the leg openings.

13. An absorbent article for personal wear about a wearer's waist, said article comprising:
    a liquid permeable bodyside liner for facing the wearer;
    an outer cover for facing away from the wearer;
    an absorbent body disposed between the liner and the outer cover;
    a front waist region, a back waist region and a crotch region extending longitudinally between and interconnecting the front and back waist regions;
    a pair of laterally opposite front side panels extending outward from the front waist region;

a pair of laterally opposite back side panels extending outward from the back waist region, the back side panels and front side panels cooperatively defining respective sides of the article;

a primary fastening system for releasably attaching the side panels extending outward from the front waist region to respective side panels extending outward from the back waist region; and a waist adjustment system comprising a tab having an attachment region which attaches the tab to one of said front side panels and said back side panels and a tab region extending transversely outward from the attachment region, the tab region having a fastener region releasably attachable to multiple locations on said one of said front side panel and said back side panel to selectively alter the size of the waist opening, wherein the fastener region of the tab is attached to said one of said front side panel and said back side panel when said front side panel and said back side panel are detached at said primary fastening system.

14. The absorbent article as set forth in claim 13 wherein at least a portion of said one of said front side panels and said back panels to which the tab is attached is cinched in a fitted, wear configuration of the article.

15. The absorbent article as set forth in claim 14 wherein the tab region of the tab comprises a grip region disposed outward of the fastener region for use in manually gripping and manipulating the tab.

16. The absorbent article as set forth in claim 13 wherein the waist adjustment system comprises two spaced-apart tabs.

17. The absorbent article as set forth in claim 13 wherein the fastener region of the tab region of the tab comprises a hook fastener.

18. The absorbent article as set forth in claim 17 wherein at least said one of said front side panels and back side panels comprises a loop fastener capable of releasable engagement with the hook fastener of the fastener region.

19. The absorbent article as set forth in claim 13 wherein the article can be folded in a compact configuration and the fastener region of the tab can be attached to one of said back waist region and crotch region to secure the article in its compact configuration.

20. The absorbent article as set forth in claim 13 wherein the primary fastening system is operable independent of the waist adjustment system.

21. The absorbent article as set forth in claim 13 wherein a portion of the primary fastening system overlays a portion of the waist adjustment system.

22. The absorbent article as set forth in claim 13 wherein a portion of the waist adjustment system underlies the primary fastening system.

23. The absorbent article as set forth in claim 13 wherein the primary fastening system releasably attaches the side panels in overlapping relationship.

24. A waist adjustment system for an absorbent article for personal wear about a wearer's waist, said article comprising a liquid permeable bodyside liner for facing the wearer, an outer cover for facing away from the wearer, an absorbent body disposed between the liner and the outer cover, a front waist region, a back waist region and a crotch region extending longitudinally between and interconnecting the front and back waist regions, an article fastening system attaching the back waist region to the front waist region to define a wear configuration of the absorbent article having a waist opening and a pair of leg openings spaced from the waist opening, the waist opening having a size in the wear configuration of the absorbent article, the waist adjustment system comprising:

a tab having an attachment region which attaches the tab to one of said front waist region and said back waist region and a tab region extending transversely outward from the attachment region, the tab region having a fastener region releasably attachable to multiple locations on said one of said front waist region and said back waist region to selectively alter the size of the waist opening in said wear configuration, wherein the fastener region attaches the tab to said one of said front waist region and said back waist region when the back waist region is detached from the front waist region at the article fastening system.

25. The waist adjustment system as set forth in claim 24 wherein the tab region of the tab comprises a grip region disposed outward of the fastener region for use in manually gripping and manipulating the tab.

26. The waist adjustment system as set forth in claim 25 wherein the grip region is non-attachable to the article.

27. The waist adjustment system as set forth in claim 24 wherein the tab comprises a substrate having a first fastening component attached thereto to define the fastener region and a second fastening component attached thereto to define a portion of the article fastening system.

28. The waist adjustment system as set forth in claim 27 wherein the first and second fastening components are on opposite surfaces of the substrate.

29. The waist adjustment system as set forth in claim 24 wherein the tab is generally non-stretchable.

30. The waist adjustment system as set forth in claim 24 wherein at least a portion of attachment region underlies the article fastening system.

\* \* \* \* \*